United States Patent [19]

Seidel et al.

[11] Patent Number: 6,153,393
[45] Date of Patent: Nov. 28, 2000

[54] ELIMINATION OF INTERFERENCE IN DIAGNOSTIC METHODS BY PEPTIDES COMPRISING D-AMINO ACIDS

[75] Inventors: Christoph Seidel, Weilheim; Helmut Lenz, Tutzing; Johann Karl, Peissenberg; Beatus Ofenloch-Hähnle, Polling; Ursula Klause, Peissenberg; Elke Faatz, Huglfing, all of Germany

[73] Assignee: Roche Diagnostics GmbH, Germany

[21] Appl. No.: 09/210,040

[22] Filed: Dec. 11, 1998

[30] Foreign Application Priority Data

Dec. 11, 1997 [DE] Germany ............................ 197 55 078
Apr. 24, 1998 [DE] Germany ............................ 198 18 383

[51] Int. Cl.$^7$ ........................ G01N 33/53; G01N 33/543; C12N 15/09; A61K 38/00; A61K 38/04

[52] U.S. Cl. ........................ 435/7.1; 435/7.92; 435/7.93; 435/7.94; 435/7.95; 435/69.3; 435/962; 436/518; 530/300; 530/330; 530/331; 530/328; 530/329; 514/12; 514/13; 514/14; 514/15; 514/16; 514/17; 514/18

[58] Field of Search ................................ 435/7.1, 7.92, 435/7.93, 7.94, 7.95, 69.3, 962; 436/518, 328, 329; 530/300, 330, 331; 514/17, 18, 12, 13, 14, 15, 16

[56] References Cited

U.S. PATENT DOCUMENTS

| | | | |
|---|---|---|---|
| 4,742,048 | 5/1988 | Bouchaudon et al. | 514/17 |
| 4,931,385 | 6/1990 | Block et al. | 435/7 |
| 5,051,356 | 9/1991 | Warren, III et al. | 436/7.34 |
| 5,599,729 | 2/1997 | Park | 437/52 |
| 5,753,628 | 5/1998 | Heavner et al. | 514/17 |

FOREIGN PATENT DOCUMENTS

| | | | |
|---|---|---|---|
| 0 260 903 A2 | 3/1988 | European Pat. Off. | G01N 33/53 |
| 0 525 916 A1 | 2/1993 | European Pat. Off. | G01N 33/50 |
| WO 91/06559 | 5/1991 | WIPO | C07K 3/06 |
| WO 95/23801 | 9/1995 | WIPO | C07D 495/04 |
| WO 96/03652 | 2/1996 | WIPO | G01N 33/533 |

OTHER PUBLICATIONS

Genzyme Pharmaceutical ; Amino acid product list, 1998.
Aldrich Chemical company; Cat No.:29,866–2, 1998.
Seidel, C., "Synthesis of a cyclic peptide for diagnostic use by oxidation of resin–bound intermediate," Peptides, pp. 236–237 (1990).
BACHEM Bioscience, Heidelberg.
Robertson, P. W., et al., Reduction in non–specific binding in enzyme immunoassays using casein hydrolysate in serum diluents, Journal of Immunological Methods, vol. 76, pp. 195–197 (1985).
Seidel, C., et al., Synthesis of a cyclic peptide for diagnostic use by oxidation of its resin–bound intermediate, Peptides, pp. 236–237 (1990).
Sieber, Peter, A new acid–labile anchor group for the solid phase synthesis of C–terminal peptide amides by the FMOC method, Tetrahedron Letters, vol. 28, No. 19, pp. 2107–2110 (1987).
Wang, Su–Sun, p–alkoxybenzyl alcohol resin and p–alkoxy-benzyloxycarbonylhydrazide resin for solid phase synthesis of protected peptide fragments, Journal of the American Chemical Society, vol. 95, No. 4, pp. 1328–1333 (1973).

*Primary Examiner*—Nita Minnifield
*Assistant Examiner*—Padma Baskar
*Attorney, Agent, or Firm*—Marilyn L. Amick; Roche Diagnostics Corporation

[57] ABSTRACT

The invention concerns the use of peptides which are comprised essentially of D-amino acids to eliminate interference in diagnostic methods, a method for eliminating interference in diagnostic methods by peptides which are comprised essentially of D-amino acids as well as a reagent that eliminates interference containing at least one peptide which is comprised essentially of D-amino acids.

26 Claims, No Drawings

ELIMINATION OF INTERFERENCE IN DIAGNOSTIC METHODS BY PEPTIDES COMPRISING D-AMINO ACIDS

The present invention concerns the use of peptides which are comprised essentially of D-amino acids to eliminate interference in diagnostic methods, a method for eliminating interference in diagnostic methods by peptides which are comprised essentially of D-amino acids as well as a reagent that eliminates interference containing at least one peptide which is comprised essentially of D-amino acids.

BACKGROUND

In the past years immunological detection methods have become very important in diagnostics. These methods enable analytes to be detected in biological samples. These analytes for example include drugs, hormones, proteins, infectious agents, microorganisms and antibodies to these analytes. These pathogens are either detected directly or indirectly in particular to detect infections by microorganisms such as bacteria, fungi or viruses. This means that, depending on the infection, the pathogen is diagnosed by an antigen test or the antibodies which have been formed specifically as an immune response to the pathogen are detected.

In all immunological detection reactions a specific binding reaction occurs between the substance which it is intended to detect (analyte) and at least one specific binding partner which specifically reacts with the analyte or specifically binds it. In this process the analyte and the specific binding partner form a specific binding pair which is in general a complex between an antigen and an antibody or an antibody fragment. In this process more than one analyte or more than one binding partner can react together in each reaction. These specific binding reactions can be detected in various ways. In general one binding partner of the specific binding reaction is labelled. Common labels are chromogens, fluorophores, substances capable of chemiluminescence or electrochemiluminescence, radioisotopes, haptens, enzyme labels or substances which in turn can form a specific binding pair such as biotin/streptavidin.

A serious problem in immunoassays is that undesired interactions and nonspecific binding reactions can take place between the specific binding partners of the immunoassay and the sample components. Such interactions usually lead to an increase of the background signal, a stronger scattering of the signals and thus a reduced sensitivity and specificity of the respective test.

Depending on the type of interference caused by nonspecific interactions, false-positive or false-negative test results can also occur.

False-negative results can occur when a substance is present in the sample which masks the analyte to be detected so that the specific detection reagents, for example an antibody, can no longer bind to the analyte.

False-positive test results are a particularly major problem. This means that a positive signal is obtained in the test although the analyte is absent. Thus, especially when diagnosing infectious diseases, the situation should not occur that samples of healthy, non-infected patients give a false-positive result in the test. In the diagnosis of HIV infections the requirements made by the approval authorities for the clinical specificity of diagnostic tests for the detection of anti-HIV antibodies is larger than 99.5%. This means that in a group of normal donors (samples from non-infected persons) no more than 5 false-positive samples may occur in 1000 samples. The false-positive reactions which nevertheless occur are caused by nonspecific substances which, depending on the test method, bind to the antigens, e.g. HIV antigens that are used for the antibody detection and then, like antibodies to the infectious agent to be detected, are falsely detected as positive by the detection system. These nonspecifically reacting substances are often antibodies. Various attempts have already been described in the prior art to reduce these nonspecific interactions in immunoassays which lead to false test results. Thus it has been known for a long time that various carbohydrate components and proteins, protein mixtures, certain protein fractions and hydrolysates thereof can reduce nonspecific interactions between the test components and the analyte in immunoassays (see for example Robertson et al., J. Immunol. Meth. 26, 1985; EP-A-0 260 903; U.S. Pat. No. 4,931,385). A disadvantage of using crude protein fractions and crude hydrolysates is that components contained therein can in turn cause other interferences of the test. Furthermore hydrolysates that are produced enzymatically can be contaminated with the proteases used for their manufacture and usually do not have a uniform quality since the enzymatic cleavage is difficult to control. Protease contaminants can attack test components and even in small amounts can lead to an impairment of the test functions and storage stability.

The use of chemically modified proteins and especially of succinylated or acetylated proteins has also been described for reducing nonspecific interactions in immunoassays (U.S. Pat. No. 5,051,356; EP-A-0 525 916). However, many of the false-positive results in antibody tests from serum samples cannot be avoided using these substances.

EP-A-0 331 068 and WO 91/06559 describe the use of polymerized immunoglobulins, in particular IgG, to reduce specific interfering factors such as e.g. rheumatoid factors. However, they do not enable the satisfactory elimination of all interfering interactions. Moreover, the addition of nonspecific human immunoglobulins in tests for human antibodies can lead to an increase of the blank value. Furthermore the isolation of human or animal IgG is complicated and expensive.

Avidin and streptavidin as well as derivatives thereof are described in WO 95/23801 as interference-eliminating agents which mainly reduce nonspecific interactions of the sample components with a streptavidin or avidin solid phase in heterogeneous immunoassays. These interference-eliminating agents cannot eliminate interference by substances that do not interact with the solid phase but rather nonspecifically bind to the usual immunological test components.

SUMMARY OF THE INVENTION

No satisfactory solution for the problem has previously been described in the prior art. The object was therefore to provide new interference-eliminating substances in order to provide a better elimination of interference by nonspecific interactions in immunoassays than was previously known in the prior art. In particular it was an object of the invention to reduce and if possible completely eliminate false test results in the diagnosis of infectious diseases.

This object is achieved by the use of peptides which are comprised essentially of D-amino acids to eliminate interference in immunological detection methods. It has surprisingly turned out that the use according to the invention of peptides which are comprised essentially of D-amino acids enables a drastic reduction of nonspecific interactions and hence a substantial avoidance of false and in particular false-positive detection reactions.

DETAILED DESCRIPTION

An important property of the peptides used as agents that eliminate interference is that these are not comprised of the naturally occurring L-amino acids but rather are comprised essentially of D-amino acids. As a result properties like hydrophilicity, flexibility and solubility are exactly imitated without the corresponding antigenic properties of the corresponding peptides comprised of L-amino acids. Hence peptides which are comprised essentially of D-amino acids are not antigenic since their steric conformation is an exact mirror image of the actual antigens. Antigenicity is understood as the specific binding behaviour towards one another of two or several immunological binding partners such as an antigen and a specific antibody. Thus the peptides comprised of D-amino acids no longer fit into the antigen binding site i.e. the paratope of the specific antibody to be detected. Hence the interference-eliminating agent according to the invention does not impede the specific detection reaction.

D-Amino acids and L-amino acids are understood as the projection formulae of amino acids according to the nomenclature of Emil Fischer for optically active (chiral) compounds. According to this the carbon chain is arranged vertically so that the end with the highest oxidation state is at the top. In addition the molecule must be arranged such that the substituents on the asymmetric C atom project towards the front. In immunoassays the notation of the configuration in amino acids relates to the amino group i.e. L-configuration for an amino group on the left and D-configuration for an amino group on the right. However, the names D and L have nothing to do with the direction of optical rotation of linearly polarized light. The D form and L form of an amino acid relate to one another like an image and a mirror image. Proteins are comprised exclusively of L-amino acids. Only some bacteria have D-amino acids in their cell wall.

The term "peptide" is understood as molecules comprised of at least two and a maximum of 100 amino acids which are linked covalently together via amide bonds. This definition applies to peptides comprised of L-amino acids as well as of D-amino acids.

Peptides comprised of L-amino acids are often used as immunological binding partners in immunoassays. These peptides used as detection reagents can, but do not have to be, labelled with other molecules. These labels include for example biotin, haptens such as digoxigenin or steroid hormones, enzymes, dyes, fluorescent labels. Peptides comprised of L-amino acids which are used as immunological binding partners bind in immunoassays specifically to another binding partner such as the analyte which in this case can be an antibody. If a labelled peptide is used, the presence of the analyte can be detected by the label of the peptide bound to the analyte. The peptides comprised of L-amino acids can also be used as competitors. In this case the peptide comprised of L-amino acids displaces one of the immunological binding partners, for example of an antigen-antibody complex, from the complex. The concentration of the analyte can be deduced based on the amount of labelled peptide either in the complex or in the solution by comparison with a standard curve.

The sequence of the peptides comprised of L-amino acids used as immunological binding partners or detection reagents is either based on the sequence of the analyte to be detected or on the sequence of an immunological binding partner which specifically binds the analyte. In this connection a defined epitope region is usually selected as a sequence region which is known to be recognized immunologically. A number of immunologically active epitopes of virus proteins have already been described especially in the field of infectious diseases such as HIV and HCV infections. The most important immunologically active regions of HIV include the envelope (env) proteins gp41, gp120 and the capsid (gag) protein p24.

However, complete proteins or fragments thereof are often used as immunological binding partners in the diagnosis of infectious diseases which have either been purified from their native source or have been produced recombinantly.

The amino acid sequence of the peptides used to eliminate interference according to the invention which are comprised essentially of D-amino acids—like the peptides comprised of L-amino acids—is based on the sequence that is either present on the analyte itself or on an analyte-specific binding partner used for the analyte detection. The sequence of the peptide used to eliminate interference preferably corresponds to the epitope on the analyte or the epitope on the specific binding partner.

If L-peptides are used as specific binding partners for the immunological reaction, then, when selecting the peptides for eliminating interference, it is preferable to select a peptide of the same length and same sequence which is completely comprised of D-amino acids.

The length of the peptides according to the invention which are comprised essentially of D-amino acids is at least 4 to 50, preferably 5 to 20 D-amino acids.

An essential feature of the peptides according to the invention is that they are not comprised of L-amino acids but rather are comprised essentially of D-amino acids. In this connection the use of glycine which possesses no asymmetric C atom and is thus neither in the D-configuration nor L-configuration is expres—ly allowed. The term "comprised essentially of D-amino acids" means a peptide, whose sequence which corresponds to the epitope on the analyte or the specific binding partner is comprised of D-amino acids. However, within the scope of the invention it is also possible that this epitope region is flanked by amino acids which have the natural L-configuration. This may be necessary when spacer regions comprised of L-amino acids are coupled to the epitope region. However, it is also possible to use other chemical groups such as alkyl chains as spacers. These spacers are often required to couple other molecules to the interference-eliminating peptide. However, in this connection it is important that the relevant epitope for eliminating interference is comprised of D-amino acids. According to the invention it is also possible that the flanking regions are comprised of lipid structures as occur for example in phospholipids or lipoproteins, or are comprised of sugar chains. The regions of the interference-eliminating peptide which flank the epitope can in principle be modified as desired. With all peptide modifications it is important that the interference-eliminating effect is not impaired. Care must also be taken that the peptide used to eliminate interference does not itself interfere with the immunoassay due to additional modifications.

The length of the peptides according to the invention described further above relates to the epitope comprised of D-amino acids. It is quite possible that the total length of the interference-eliminating peptide exceeds the upper limit of 50 amino acids due to the incorporation of flanking sequences.

Peptides which are comprised essentially of D-amino acids are produced by chemical synthesis on a solid phase, preferably using a commercial peptide synthesizer. The synthesis is preferably carried out according to the Merrifield method familiar to a person skilled in the art. In this process the individual amino acid building blocks must be used as D-isomers in those places where this is required. The other process steps correspond to the synthesis of peptides from L-amino acids. This means that the synthesis is carried out according to known methods, preferably starting at the carboxyl end of the peptide using amino acid derivatives (in this case: D-amino acid derivatives). Amino acid derivatives are preferably used whose amino end group required for coupling is derivatized with a fluorenylmethyloxy-carbonyl (Fmoc) residue. Reactive side groups of the amino acids used contain protective groups which can be readily cleaved after completion of the peptide synthesis. Preferred examples of this are protective groups such as triphenylmethyl(Trt), t-butylether (tBu), t-butylester (OtBu), ter.-butyloxycarbonyl (Boc) or 2,2,5,7,8-pentamethylchroman-6-sulfonyl (Pmc).

For the peptide synthesis it is possible to use the 19 standard amino acids in the D form which naturally occur in the L form. In addition it is also possible to use the D forms of amino acid derivatives such as 4-hydroxyproline, 5-hydroxylysine, 3-methylhistidine, homoserine or ornithine.

After completion of the synthesis and optionally after releasing the peptide from the solid phase, the protective groups are cleaved by methods known to a person skilled in the art such as by addition of acif. Afterwards the product obtained in this manner is purified, preferably by HPLC.

If the inventive peptides synthesized in this manner contain an intramolecular disulfide bridge, the disulfide bridge is formed before releasing the peptide by oxidation on the solid phase with iodine in hexafluoroisopropanol/dichloromethane (Seidel C., in Giralt and Andreu, Eds., Peptides 1991, Escom, Leiden, p. 236).

It is also possible to use a standardized synthesis and purification process to prepare the peptides according to the invention which are comprised essentially of D-amino acids. Complicated apparatuses or laborious purification of the interference-eliminating peptides is avoided.

The peptides which are comprised essentially of D-amino acids can be used in a monomeric form. This means that each peptide contains a single epitope that is to be freed of interference in the form of D-amino acids. According to the invention it is possible to use several different peptides with different epitopes which are comprised essentially of D-amino acids to eliminate interference. This may be expedient if an analyte has several immunologically recognizable epitopes or if different analytes are detected in one test.

The peptides according to the invention used to eliminate interference can, however, carry the corresponding epitope several times i.e. as a multimer. Hence they can also be used as polyhaptens. This means that the peptides according to the invention are coupled several times to a carrier to produce a polyhapten the components of which are comprised essentially of D-amino acids. In this connection it is also possible to couple several peptides according to the invention which are comprised essentially of D-amino acids to a carrier. A macromolecule which does not itself participate in the immunological reaction can serve as the carrier such as a large protein like bovine serum albumin, particles made of latex, polystyrene, gold or dextran. The polyhaptens can be produced analogously to the method described in WO 96/03652. D-amino acids are then used instead of the L-amino acids described in this patent for the production of the polyhaptens according to the invention.

It has surprisingly turned out that the use of such polyhaptens in which the peptides which are comprised essentially of D-amino acids are coupled to a carrier material enables a substantial avoidance of false-positive reactions in immunoassays. The peptides according to the invention are therefore preferably used in the form of polyhaptens to eliminate interference in immunoassays. The interference-eliminating effect increases with increasing epitope density. This means that the interference-eliminating effect increases from a monomeric peptide to the polyhapten.

The peptides according to the invention which are comprised essentially of D-amino acids are added to the test mixture as interference-eliminating agents in immunoassays. This substantially avoids nonspecific binding and reactions that occur in immunological tests such as antibody tests by reaction of nonspecific antibodies with the detection antigens. A possible explanation for the interference-eliminating effect of the peptides according to the invention may be that the interference-eliminating peptides bind to the nonspecific antibodies but not to the specific antibodies to be detected. The interference-eliminating peptides which are comprised essentially of D-amino acids lack the actual antigenicity. Apparently this is exactly why they are able to eliminate interference. It is possible that the "false" nonspecific reaction of the interfering nonspecific antibodies is a result of binding via its antigen binding site, the paratope, to the antigen used as the detection reagent. It is, however, also possible that a site different to the paratope of the antibody reacts with the antigens. The antibodies blocked in this manner with the interference-eliminating agent can then no longer react with the detection antigens with the result that fewer or in the ideal case no false-positive results occur.

Some interfering substances have the property of directly binding to the solid phase. If the interference-eliminating peptide according to the invention is now used, this can practically glue up the binding sites of the interfering substance and therefore puts the immunological reaction out of reach of the interfering agent.

In some immunological tests false-negative test results also occur. This may be due to the fact that an interfering antibody in the sample binds to the antibody to be detected in such a manner that it masks its antigen binding site. As a result this sample antibody is removed from the actual immunological reaction in antibody tests and a false-negative result occurs. In such a case the object of an interference-eliminating agent is to bind to the interfering antibody or the interfering substance in such a way that this is masked. The use of the peptides according to the invention which are comprised essentially of D-amino acids to avoid false-negative test results is also a subject matter of the present invention.

The peptides according to the invention which are comprised essentially of D-amino acids are preferably used in an excess over the interfering substance present in the sample. There is an upper limit to the use of the peptides according to the invention only in as much as the solubility of the interference-eliminating agent must be ensured in the test mixture. The amount or the concentration of the peptides used to eliminate interference which ace comprised essentially of D-amino acids or of the corresponding polyhaptens depends on the interfering substance which is in a sample. This means that depending on the extent of interference, an amount of interference-eliminating reagent must be added which has to be individually determined by a person skilled in the art depending on the test procedure. A range from 1 nmol/l to 1 mol/l has proven to be an appropriate concentration range.

According to the invention the use of the peptides according to the invention preferably does not influence the sensitivity of the test.

The peptides according to the invention which are comprised essentially of D-amino acids enable in principle the elimination of interference in all immunoassay formats familiar to a person skilled in the art so that false and in particular false-positive test results are largely avoided.

The peptides according to the invention can be used in all test formats provided an immunologically active binding partner is present in the test mixture i.e. in the sample or in the detection reagents. The peptides according to the invention are used in heterogeneous or homogeneous methods but preferably in heterogeneous methods.

A solid phase is always involved in heterogeneous methods to which the complex that forms of analyte and the binding partner or partners binds. An example of this is an antibody test in a bridge test format as described in EP-A-280 211. In this case a first binding partner such as an antigen which can specifically bind to the antibody to be determined is bound to a solid phase. The analyte-antibody to be determined binds to the solid phase bound antigen. A further specific binding partner (antigen) for the analyte is additionally present in the test mixture which is provided with a label. As soon as the bridge is formed comprised of solid phase-bound binding partner, analyte antibody and labelled binding partner, the solid phase is separated from the liquid phase and the label is detected in the solid or the liquid phase. The peptides according to the invention which are comprised essentially of D-amino acids have the effect in this format that nonspecific substances in the sample such as nonspecific antibodies are masked in such a way that they can no longer participate in the formation of the solid phase-bound immune complex. Hence in particular false-positive test results are substantially avoided.

Another format which can be freed of interference according to the invention is the competitive test procedure in which a solid phase-bound complex of two binding partners that are specific for one another is formed in which the binding partner that is not directly coupled to the solid phase is labelled. The analyte which is an antigen or an antibody depending on the test procedure, displaces the labelled binding partner from the complex depending on the concentration. After separation of the solid from the liquid phase, the label is detected in one of the phases. The peptides according to the invention also block in this case the nonspecific binding of interfering sample substances to the binding partners used as detection reagents and substantially prevent false test results.

Other formats which can be freed of interference according to the invention are the classical antigen detection in a sandwich format in which the analyte (in this case an antigen) is bound in a sandwich between a solid phase-bound and a labelled antibody, and the indirect detection of an analyte-antibody by its binding to a solid phase-bound antigen. In this case the detection is carried out by binding a further labelled antibody to the analyte antibody.

Of course combined test formats in which for example an antigen of a virus and an antibody directed against a viral protein of the virus are detected simultaneously can also be freed of interference according to the invention.

The elimination of interference in homogeneous test formats is also conceivable. In homogeneous test procedures specific binding partners (antibodies or antigens) are generally cross-linked with an analyte which only takes place in the presence of the analyte. Alternatively it is also possible to destroy already pre-cross-linked antigen-antibody complexes by adding the analyte since the analyte competes with the antigen (an analyte analogue) or the antibody. In each case the turbidity or the change in the turbidimetric density is measured after addition of analyte. An interfering substance which cross-links the haptens or antigens that are provided instead of the true analyte-antibody simulates a false-positive reaction. Also in this case it is possible to substantially avoid false-positive results by using the peptides according to the invention which are comprised essentially of D-amino acids.

The said test formats as well as the detection of the analytes are familiar to a person skilled in the art and do not need any further explanation here.

A further subject matter of the invention is an immunological method for the detection of an analyte in a sample in a known test format which is characterized in that peptides which are comprised essentially of D-amino acids are added to the reaction mixture to eliminate interference. In the method according to the invention the sample is in general contacted with one or several binding partners that are specific for the analyte and with the peptides according to the invention to eliminate interference. In this process the sample can be contacted with the peptides used to eliminate interference before adding or at the same time as adding the specific binding partner. Subsequently the complex formed from analyte and specific binding partner is determined as a measure of the presence of the analyte.

The test formats for carrying out the immunological method for detecting an analyte have been exemplified in more detail in one of the above sections and moreover are general technical knowledge to a person skilled in the art.

All substances can serve as an analyte which react specifically with at least one specific binding partner to form a complex such as haptens, antigens, antibodies or nucleic acids.

Suitable samples for carrying out immunoassays which are to be freed of interference according to the invention are all biological fluids familiar to a person skilled in the art. Body fluids such as whole blood, blood serum, blood plasma, urine or saliva are preferably used as the sample.

In addition to the so-called wet tests in which the test reagents are present in a liquid phase, all common dry test formats can also be used that are suitable for the immunological detection of analytes. In these dry tests or test strips as described for example in EP-A-0 186 799 the test components are applied to a carrier. The peptides according to the invention which are comprised essentially of D-amino acids are then already applied to the dry test strip before the immunological detection.

The interference-eliminating agents according to the invention should preferably be already added to the sample in wet tests before the binding partners used as the detection reagents are added so that the interfering nonspecific substances can react with the interference-eliminating agent i.e. can bind to it. It has proven to be appropriate to already add the peptides according to the invention which are comprised essentially of D-amino acids to the sample buffer which is used to dilute the samples. The peptides according to the invention are preferably also added to the detection reagents.

The invention also concerns a method for eliminating interference in diagnostic detection methods which is characterized in that peptides which are comprised essentially of D-amino acids are added to the reaction mixture. The preferred methods which are to be freed of interference according to the invention include immunodiagnostic detection methods of infectious diseases, especially of viral origin. These include, among others, tests for anti-HIV antibodies, HIV antigens, combined anti-HIV/HIV antigen tests, anti-HCV antibodies, HCV antigens, combined anti-HCV/HCV antigen tests.

A further subject matter of the invention is an interference-eliminating reagent containing at least one peptide which is comprised essentially of D-amino acids. Further potential components of the interference-eliminating reagent are buffers, salts and detergents familiar to a person skilled in the art. The interference-eliminating reagent can be prepared in a liquid, aqueous form or lyophilized form.

The invention is further elucidated by the following examples.

EXAMPLE 1

Production of an Interference-eliminating Reagent (I) Based on a Peptide

The D-peptide for producing the interference-eliminating reagent was synthesized by means of fluorenylmethyloxycarbonyl-(Fmoc) solid phase peptide synthesis on a batch peptide synthesizer ABI A413. For this 4.0 equivalents in each case of the amino acid derivatives 1. to 16. (BACHEM Bioscience, Heidelberg) shown in Table 1 were used:
Table 1:
1. Fmoc-D-Val-OH
2. Fmoc-D-Ala-OH
3. Fmoc-D-Thr(-OtBu)-OH
4. Fmoc-D-Thr(-OtBu)-OH
5. Fmoc-D-Cys(Trt)-OH
6. Fmoc-D-Ile-OH
7. Fmoc-D-Leu-OH
8. Fmoc-D-Lys(-Boc)-OH
9. Fmoc-Gly-OH
10. Fmoc-D-Ser(Boc)-OH
11. Fmoc-D-Cys(Trt)-OH
12. Fmoc-Gly-OH
13. Fmoc-D-Trp(-Boc)-OH
14. Fmoc-D-Iso-OH
15. Fmoc-Gly-OH
16. Fmoc-D-Leu-OH
17. Fmoc-β-Ala-OH
18. Fmoc-ε-aminocaproic acid
19. Fmoc-β-alanine
20. Boc-L-Lys(-Fmoc)-OH
21. Fmoc-L-Cys(-Trt)-OH The D-amino acids derivatives were dissolved in N-methylpyrrolidone. The D-peptide was synthesized on 400 mg 4-(2',4'-dimethoxyphenyl-Fmoc-aminomethyl)-phenoxy resin (Tetrahedron Letters 28, 1987, p. 2107) at a loading of 0.47 mmol/g (JACS 95, 1973, p. 1328). The coupling reactions were carried out for 20 min with in each case 4 equivalents N-hydroxybenzotriazole and dicyclohexylcarbodiimide in dimethylformamide as the reaction medium. After each coupling step the Fmoc group was cleaved off within 20 min by means of 20% piperidine in dimethylformamide.

Before releasing the peptide, the disulfide bridge was formed by oxidation on the solid phase with iodine in hexafluoroisopropanol/dichloromethane (Seidel C., in Giralt E. and Andreu D. (eds.) Peptides 1991, Escom, Leiden p. 236).

The peptide was released from the resin and the permanent protective groups were cleaved off by means of 20 ml trifluoroacetic acid, 0.5 ml ethanedithiol, 1 ml thioanisole, 1.5 ml phenol and 1 ml water within 40 min at room temperature. Subsequently 300 ice-cold diisopropyl ether was added to the reaction solution and kept for 40 min at 0° C. to completely precipitate the peptide. The precipitate was removed by filtration, re-washed with diisopropyl ether and dissolved in a small amount of 50% acetic acid and lyophilized. The crude peptide obtained was purified within ca. 120 min by means of preparative HPLC on RP 18-column material using a gradient of acetonitrile/water containing 0.1% trifluoroacetic acid. The identity of the eluted pure material was checked with ionspray mass spectrometry.

EXAMPLE 2

Production of an Interference-eliminating Reagent (II) and (III) Based on a Polypeptide Conjugate A D-peptide capable of coupling named HIV, gp41P2(D)-Cys(I) is produced by additionally N-terminally attaching a spacer such as e.g. long chain-like ω-alkyl-amino acids and a cysteine by means of solid phase peptide chemical methods before releasing the peptide from the resin. In this case the amino acids 17. to 21. of Table 1 are used. However, oxidation is carried out before introducing the spacer amino acids and the cysteine.

In order to prepare the conjugate, bovine serum albumin was firstly reacted with a 12-fold molar amount of N-maleinimidohexanoyl-N-hydroxysuccinimide (MHS). The reaction was carried out in 0.1 mol/l potassium phosphate buffer pH 7.0 and a protein concentration of 10 mg/ml within 120 min. The low molecular components of the reaction were separated by means of gel permeation chromatography (AcA 202-Gel, Biorad). As a result about 6 of the primary amino groups of the lysine side chains were modified with maleinimido groups.

The D-peptide was reacted within 120 min with the maleinimido-functionalized bovine serum albumin in 0.1 mol/l potassium phosphate buffer pH 7.0. Separation of non-reacted peptide and the separation of monomeric and polymeric conjugate was carried out on Sephacryl-S200 HR. In a typical reaction in 20.8 ml buffer of 206 mg activated protein with 102 mg HIV, gp41P2(D)-Cys peptide (I), 27.7 mg polymeric (II) and 76.3 mg monomeric dissolved protein conjugate (III) are obtained. The solution is admixed with trehalose in a 40-fold ratio and lyophilized.

EXAMPLE 3

Elimination of Interference in an Immunoassay for the Detection of Anti-HIV Antibodies in a Microspot® Format Microspot® is a miniaturized ultrasensitive technology which is ideally suitable for the simultaneous determination of different diagnostic parameters in a single measurement process. The underlying technology is described for example in the U.S. Pat. No. 5,599,729.

The test described here as an example is carried out in the so-called bridge test format in which two antigens are bridged together by the sample antibody to be detected. In the case of the determination of anti-HIV antibodies (also named <HIV> antibodies), the individual HIV antigens are immobilized in so-called arrays on a polystyrene carrier. The individual HIV antigens are applied as spots on the test zone by means of a technology related to ink-jet technology. In the test procedure 30 μl of sample (for example blood serum) prediluted with sample buffer is pipetted onto the test zone and incubated for 20 minutes at room temperature while shaking. After aspirating the sample and washing the test zone with wash buffer, 30 μl reagent solution 1 which contains a mixture of all digoxigenin-labelled HIV antigens is pipetted onto the test zone and again incubated for 20 min at room temperature while shaking. The sequences of the immobilized antigens correspond to the sequences of the 5 digoxigenin labelled HIV antigens present in reagent solution 1. After aspirating reagent solution 1 and washing the test zone with wash buffer, 30 μl reagent solution 2 which contains the detection reagent is pipetted onto the test zone. Fluorescent dyed latex particles of 100 nm in size are used as the detection reagent which are covalently coated with an anti-digoxigenin antibody.

This detection reagent is in turn incubated for 20 min at room temperature while shaking, subsequently aspirated, washed and sucked dry. The test zone is irradiated with a He—Ne laser at 633 nm wavelength and the fluorescence at 670 nm wavelength is measured with a CCD camera.

Sample buffer:

50 mM Tris pH 7.6

0.05% Tween 20

0.5% BSA 0.1% B-IgG 0.01% MIT

Reagent solution 1:

(Boehringer Mannheim GmbH, Order No. 1650807, Enzymun <HCV> incubation buffer)

50 mM Na phosphate buffer 120 mM NaCl 0.01% MIT

20% PDB

In the Microspot® <HIV> assay two different peptides which represent two different epitopes of the gp41 antigen are applied. In the screening of ca. 500 negative samples, 4 samples were detected as false-positive. It was noticeable that all 4 samples react nonspecifically with the gp41 peptide 2 antigen spot whereas all other spots exhibited no reaction. Despite all optimization measures such as optimizing raw materials and buffers, it was not possible to improve the specificity. It was not until a peptide of identical sequence which was synthesized from D-amino acids was added that a complete elimination of interference in 3 of the 4 samples was achieved. The best elimination of interference was achieved by using a polymeric interference-eliminating molecule (II) i.e. a polyhapten which contains 6 HIV, gp41P2(D) molecules per BSA carrier molecule (see Tables 2 and 3):

TABLE 2

Results with sample and reagent 1 buffer without interference-eliminating reagent on the gp-41 peptide 2 spot:

| sample | background* [counts] | signal gp41-P2- [counts] | signal gp41-P2 background | cut-off index** |
|---|---|---|---|---|
| negative control | 33 | 33 | 0 | 0.0 |
| positive control | 57 | 2642 | 2585 | 39.2 |
| positive sample 1 | 145 | 26685 | 26540 | 402.1 |
| positive sample 2 | 55 | 3158 | 3103 | 47.0 |
| interfering sample 1 | 43 | 980 | 937 | 14.2 |
| interfering sample 2 | 28 | 767 | 739 | 11.2 |
| interfering sample 3 | 35 | 877 | 842 | 12.8 |
| interfering sample 4 | 37 | 204 | 167 | 2.5 |
| negative sample | 29 | 29 | 0 | 0.0 |

*background corresponds to signals next to the test zones
**cut-off index = signal$_{sample}$ − signal$_{background}$/2×signal$_{negative\ control}$

TABLE 3

Results with interference-eliminating reagent (100 μg/ml in the sample buffer and 10 μg/ml in the reagent 1 buffer) on the gp41 peptide 2 spot:

| sample | background* [counts] | signal gp41-P2- [counts] | signal gp41-P2 background | cut-off index** |
|---|---|---|---|---|
| negative control | 28 | 28 | 0 | 0.0 |
| positive control | 53 | 2258 | 2205 | 39.4 |
| positive sample 1 | 115 | 25951 | 25836 | 461.4 |
| positive sample 2 | 57 | 2650 | 2593 | 46.3 |
| interfering sample 1 | 42 | 152 | 110 | 2.0 |
| interfering sample 2 | 26 | 26 | 0 | 0.0 |
| interfering sample 3 | 30 | 30 | 0 | 0.0 |
| interfering sample 4 | 34 | 34 | 0 | 0.0 |

*background corresponds to signal next to the test zones
**cut-off index = signal$_{sample}$ − signal$_{background}$/2×signal$_{negative\ control}$ This result shows that 4 samples strongly interfere with the Microspot® <HIV> test and that these produce a false-positive result. The addition of the interference-eliminating reagent according to the invention to the sample and reagent 1 buffer enabled an unequivocal elimination of interference in 3 of the 4 samples whereas the interfering signal of the 4th sample is considerably reduced. It is surprising that the signals of the positive samples are not reduced or only to a minimum extent so that the sensitivity of the test is completely retained.

What is claimed is:

1. A method for detecting an analyte in a sample suspected of containing said analyte, said method comprising the steps of:
   a. forming a reaction mixture comprising:
      i. said sample,
      ii. a binding partner specific for said analyte, said binding partner forming a complex with said analyte, and
      iii. a peptide comprising essentially D-amino acids, said peptide further comprising an amino acid sequence corresponding to an epitope selected from the group consisting of epitopes of said analyte and said binding partner, said peptide being in an amount sufficient to reduce interference from nonspecific binding reactions; and
   b. measuring the complex formed in said reaction mixture as a measure of said analyte.

2. The method of claim 1, wherein said peptide has a length of between 4 and 50 amino acids.

3. The method of claim 1, wherein said analyte is selected from the group consisting of antibodies and antigens of viral origin.

4. The method of claim 1, wherein said analyte is selected from the group consisting of HIV antibodies, HIV antigens, HCV antibodies and HCV antigens.

5. The method of claim 1, wherein said peptide is present as a polyhapten comprising multiples of said peptide coupled to a carrier.

6. The method of claim 5, wherein said carrier is selected from the group consisting of bovine serum albumin and particles of latex, polystyrene, gold and dextran.

7. The method of claim 1, wherein said peptide is added in an amount from 1 nmol/l to 1 mol/l.

8. The method of claim 1, wherein said method is a heterogeneous immunoassay.

9. The method of claim 1, wherein said method is a homogeneous immunoassay.

10. The method of claim 1, wherein said method is a competitive immunoassay.

11. The method of claim 1, wherein said method is an immunoassay based on the bridge test principle.

12. The method of claim 1, wherein said method is an immunoassay based on the sandwich test principle.

13. The method of claim 1, wherein said method is an immunoassay based on the indirect test principle.

14. A method for eliminating interference from nonspecific binding reactions in a diagnostic assay, said assay involving the reaction, in a reaction mixture, of an analyte with a binding partner specific for said analyte, said method comprising including in said reaction mixture a peptide comprising essentially D-amino acids, said peptide comprising an amino acid sequence corresponding to an epitope selected from the group consisting of epitopes of said analyte and said binding partner and further being added in an amount sufficient to reduce interference from nonspecific binding reactions.

15. The method of claim 14, wherein said peptide has a length of between 4 and 50 amino acids.

16. The method of claim 14, wherein said analyte is selected from the group consisting of antibodies and antigens of viral origin.

17. The method of claim 14, wherein said analyte is selected from the group consisting of HIV antibodies, HIV antigens, HCV antibodies and HCV antigens.

18. The method of claim 14, wherein said peptide is present as a polyhapten comprising multiples of said peptide coupled to a carrier.

19. The method of claim 18, wherein said carrier is selected from the group consisting of bovine serum albumin and particles of latex, polystyrene, gold and dextran.

20. The method of claim 14, wherein said peptide is added in an amount from 1 nmol/l to 1 mol/l.

21. The method of claim 14, wherein said method is a heterogeneous immunoassay.

22. The method of claim 14, wherein said method is a homogeneous immunoassay.

23. The method of claim 14, wherein said method is a competitive immunoassay.

24. The method of claim 14, wherein said method is an immunoassay based on the bridge test principle.

25. The method of claim 14, wherein said method is an immunoassay based on the sandwich test principle.

26. The method of claim 14, wherein said method is an immunoassay based on the indirect test principle.

* * * * *